United States Patent
Verma et al.

(10) Patent No.: US 10,258,622 B2
(45) Date of Patent: *Apr. 16, 2019

(54) METHOD OF TREATING COLORECTAL CANCER BY ADMINISTRATION OF PHARMACEUTICAL FORMULATIONS OF (S)-METHYL (1-((4-(3-(5-CHLORO-2-FLUORO-3-(METHYLSULFONAMIDO) PHENY1)-1-ISOPROPYL-1H-PYRAZOL-4-YL)PYRIMIDIN-2-YL)AMINO)PROPAN-2-YL) CARBAMATE

(71) Applicant: Array BioPharma, Inc., Boulder, CO (US)

(72) Inventors: Daya Verma, Edison, NJ (US); Yogita Krishnamachari, Springfield, NJ (US); Xiaohong Shen, Livingston, NJ (US); Hanchen Lee, Teaneck, NJ (US); Ping Li, Basking Ridge, NJ (US); Rajinder Singh, Sewaren, NJ (US); LayChoo Tan, Bridgewater, NJ (US)

(73) Assignee: Array BioPharma Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/452,239

(22) Filed: Mar. 7, 2017

(65) Prior Publication Data
US 2017/0202837 A1    Jul. 20, 2017

Related U.S. Application Data

(63) Continuation of application No. 15/179,190, filed on Jun. 10, 2016, now Pat. No. 9,763,941, which is a
(Continued)

(51) Int. Cl.
*A61K 31/506* (2006.01)
*A61K 9/20* (2006.01)
(Continued)

(52) U.S. Cl.
CPC .......... *A61K 31/506* (2013.01); *A61K 9/0053* (2013.01); *A61K 9/2013* (2013.01);
(Continued)

(58) Field of Classification Search
CPC .. A61K 31/506; A61K 9/2013; A61K 9/2027; A61K 9/2031; A61K 9/4858; A61K 9/4866
See application file for complete search history.

(56) References Cited

U.S. PATENT DOCUMENTS

| | | |
|---|---|---|
| 5,717,100 A | 2/1998 | Selnick et al. |
| 6,037,136 A | 3/2000 | Beach et al. |

(Continued)

FOREIGN PATENT DOCUMENTS

| | | |
|---|---|---|
| EP | 2018851 | 1/2009 |
| JP | 2009-504796 | 2/2009 |

(Continued)

OTHER PUBLICATIONS

"A Study of ARRY-438162 in Patients with Rheumatoid Arthritis," ClinicalTrials.gov, last updated Aug. 29, 2012, retrieved on Apr. 12, 2014, http://www.clinicaltrials.gov/ct2/show/NCT00650767?term=Arthritis&recr=Open, 3 pages.

(Continued)

*Primary Examiner* — Savitha M Rao
(74) *Attorney, Agent, or Firm* — Fish & Richardson P.C.

(57) ABSTRACT

This invention relates to solid oral pharmaceutical formulations of (S)-methyl (1-((4-(3-(5-chloro-2-fluoro-3-(methyl-sulfonamido)phenyl)-1-isopropyl-1H-pyrazol-4-yl)pyrimidin-2-yl)amino)propan-2-yl)carbamate (COMPOUND A) and the use of these formulations for treating proliferative diseases, such as solid tumor diseases.

22 Claims, 3 Drawing Sheets

Related U.S. Application Data continuation of application No. 14/359,121, filed as application No. PCT/US2012/066185 on Nov. 21, 2012, now Pat. No. 9,387,208.

(60) Provisional application No. 61/563,229, filed on Nov. 23, 2011.

(51) Int. Cl.
*A61K 9/28* (2006.01)
*A61K 9/48* (2006.01)
*A61K 9/00* (2006.01)

(52) U.S. Cl.
CPC .......... *A61K 9/2027* (2013.01); *A61K 9/2031* (2013.01); *A61K 9/282* (2013.01); *A61K 9/284* (2013.01); *A61K 9/2866* (2013.01); *A61K 9/485* (2013.01); *A61K 9/4858* (2013.01); *A61K 9/4866* (2013.01)

(56) References Cited

U.S. PATENT DOCUMENTS

| | | | |
|---|---|---|---|
| 6,204,467 | B1 | 3/2001 | Greenholtz, Jr. et al. |
| 6,268,391 | B1 | 7/2001 | Dickerson et al. |
| 6,358,932 | B1 | 3/2002 | Monia et al. |
| 6,391,636 | B1 | 5/2002 | Monia et al. |
| 6,458,813 | B1 | 10/2002 | Mantlo et al. |
| 6,911,446 | B2 | 6/2005 | Tang et al. |
| 7,482,367 | B2 | 1/2009 | Alkawa et al. |
| 8,501,758 | B2 | 8/2013 | Huang et al. |
| 8,541,575 | B2 | 9/2013 | Pulici et al. |
| 8,791,265 | B2 | 7/2014 | Pulici et al. |
| 8,946,250 | B2 | 2/2015 | Pulici et al. |
| 9,114,137 | B2 | 8/2015 | Pulici et al. |
| 9,314,464 | B2 | 4/2016 | Huang et al. |
| 9,387,208 | B2 | 7/2016 | Verma et al. |
| 2001/0006974 | A1 | 7/2001 | Byrd et al. |
| 2002/0137774 | A1 | 9/2002 | Riedl et al. |
| 2010/0022543 | A1 | 1/2010 | Melvin |
| 2010/0098763 | A1 | 4/2010 | Bechtold |
| 2010/0311751 | A1 | 12/2010 | Schmitt |
| 2011/0046370 | A1 | 2/2011 | Sim et al. |
| 2013/0053419 | A1 | 2/2013 | Pulici et al. |
| 2013/0217715 | A1 | 8/2013 | Pulici et al. |
| 2013/0296318 | A1 | 11/2013 | Huang et al. |
| 2014/0005150 | A1 | 1/2014 | Pulici et al. |
| 2015/0283136 | A1 | 10/2015 | Gallagher et al. |
| 2016/0120866 | A1 | 5/2016 | Huang et al. |
| 2016/0122324 | A1 | 5/2016 | Huang et al. |
| 2016/0263113 | A1 | 9/2016 | Huang et al. |
| 2016/0279129 | A1 | 9/2016 | Verma et al. |
| 2016/0280686 | A1 | 9/2016 | Huang et al. |
| 2016/0280687 | A1 | 9/2016 | Huang et al. |

FOREIGN PATENT DOCUMENTS

| | | |
|---|---|---|
| JP | 2010-533711 | 10/2010 |
| JP | A 2011-515371 | 5/2011 |
| JP | A 2011-528698 | 11/2011 |
| JP | A 2012-512837 | 6/2012 |
| JP | A 2012-530099 | 11/2012 |
| JP | A 2013-503139 | 1/2013 |
| JP | 5475888 | 4/2014 |
| WO | WO 1998/52940 | 11/1998 |
| WO | WO 2000/31063 | 6/2000 |
| WO | WO 2002/22577 | 3/2002 |
| WO | WO 2003/055860 | 7/2003 |
| WO | WO 2005/068452 | 7/2005 |
| WO | WO 2005/123719 | 12/2005 |
| WO | WO 2007/021966 | 2/2007 |
| WO | WO 2007/022956 | 3/2007 |
| WO | WO 2007/024843 | 3/2007 |
| WO | WO 2007/105058 | 9/2007 |
| WO | WO 2007/123892 | 11/2007 |
| WO | WO 2008/042639 | 4/2008 |
| WO | WO 2008/045627 | 4/2008 |
| WO | WO 2009/016460 | 2/2009 |
| WO | WO 2009/050291 | 4/2009 |
| WO | WO 2009/062676 | 5/2009 |
| WO | WO 2009/115572 | 9/2009 |
| WO | WO 2009/137391 | 11/2009 |
| WO | WO 2010/010154 | 1/2010 |
| WO | WO 2010/034838 | 4/2010 |
| WO | WO 2010/056662 | 5/2010 |
| WO | WO 2010/088336 | 8/2010 |
| WO | WO 2010/100127 | 9/2010 |
| WO | WO 2011/025927 | 3/2011 |
| WO | WO 2011/092088 | 8/2011 |
| WO | WO 2011/126903 | 10/2011 |
| WO | WO 2012/128709 | 9/2012 |
| WO | WO 2012/174061 | 12/2012 |

OTHER PUBLICATIONS

"MEK Inhibitor MSC1936369B Plus FOLFIRI in Second Line K-Ras Mutated Metastatic Colorectal Cancer (mCRC)," ClinicalTrials.gov, last updated Oct. 21, 2013, retrived on Apr. 12, 2014, http://cliical trials.gov/ct2/show/NCT01085331?term-MS C1936369B &rank=1, 4 pages.

Arnold, "Synthetische Reaktionen Von dimethylformamid XVL* Formylierung Von y-Picolin," Coll. Czech. Chem. Commun., 1963, 28:863 (English Abstract).

Cohen et al., "BRAF Mutation in Papillary Thyroid Carcinoma," J. Natl. Cancer Inst., 2003, 95:625-627.

Cohen, "The development and therapeutic potential of protein kinase inhibitors," Current Opinion in Chemical Biology, 1999, 3:459-465.

Culbertson et al., "New 7-substituted quinolone antibacterial agents. The synthesis of 1-ethyl-I,4-dihydro-4-oxo-7-(2-thiazolyl and 4-thiazolyl)-3-quinolinecarboxylic acids," J. Heterocycl. Chem, 1987, 24:1509.

Davies et al., "Mutations of the BRAF Gene in Human Cancer," Nature, 2002, 417:949-954.

Dhirendra et al., "Solid dispersions: A review," Pak. J. Pharm Sci, Apr. 2009, 22(2):234-246.

Fremin and Meloche, "From basic research to clinical development of MEK 1/2 inhibitors for cancer therapy," J. Hematology and Oncology, 2010, 3:8.

Goodacre et al., "Imidazo[1,2-a]pyrimidines as Functionally Selective and Orally Bioavailable GABAxA[alpha]2/ [alpha]3 binding Site Agonists for the Treatment of Anxiety Disorders," J. Med. Chem., 2006, 49(1):35-38.

Grimm et al., "A New Strategy for the Synthesis of Benzylic Sulfonamides: Palladium-Catalyzed Arylation and Sulfonamide Metathesis," J. Org. Chem, 2007, 72(21):8135-8138.

Hagemann and Rapp, "Isotope-specific functions of Raf kinases," Expt. Cell Res., 1999, 253:34-46.

Hingorani et al., "Suppression of BRAFV599E in Human Melanoma Abrogates Transformation," Cancer Res., 2003, 63:5198-520.

Hoshino et al., "Constitutive activation of the 41-/43-kDa mitogen-activated protein kinase signaling pathway in human tumors," Oncogene, 1999, 18:813-822.

International Preliminary Report on Patentability in International Application No. PCT/EP2009/0595506, dated Jan. 25, 2011, 6 pages.

International Preliminary Report on Patentability in International Application No. PCT/EP2011/050654, dated Jul. 31, 2012, 6 pages.

International Preliminary Report on Patentability in International Application No. PCT/EP2013/073452, dated May 12, 2015, 7 pages.

International Preliminary Report on Patentability in International Application No. PCT/US2010/046930, dated Feb. 28, 2012, 8 pages.

International Preliminary Report on Patentability in International Application No. PCT/US2012/066185, dated, May 27, 2014, 8 pages.

(56) References Cited

OTHER PUBLICATIONS

International Report on Patentability in International Application No. PCT/EP2011/063325, dated Feb. 5, 2013, 8 pages.
International Search Report and Written Opinion in International Application No. PCT/US2012/066185, dated Mar. 5, 2013, 13 pages.
International Search Report in International Application No. PCT/EP2009/059506, dated Sep. 23, 2009, 3 pages.
International Search Report in International Application No. PCT/EP2011/050654, dated Apr. 6, 2011, 4 pages.
International Search Report in International Application No. PCT/EP2011/063325, dated Aug. 31, 2011, 3 pages.
International Search Report in International Application No. PCT/EP2013/073452, dated Dec. 13, 2013, 5 pages.
International Search Report in International Application No. PCT/US2010/046930, dated Oct. 19, 2010, 5 pages.
Japanese Preliminary Examination Report in Japanese Application No. 2014-098022, dated Nov. 18, 2015, 5 pages (with English Translation).
Kolch et al., "The role of Raf kinases in malignant transformation," Exp. Rev. Mol. Med, http://citeseerx.ist.psu.edu/viewdoc/download?doi=10.1.1.114.8626&rep=rep1&type=pdf, Apr. 25, 2002,18 pages.
Lai et al., "Cotargeting histone deacetylases and oncongenic BRAF synergistically kills human melanoma cells by necrosis independently of RIPK1 and RIPK3," Cell Death and Disease, 2013, 4:e655, 13 pages.
Mccubrey et al., "Emerging MEK inhibitors," Expert Opinion Emerging Drugs, Inform Healthcare, 2010, 15(2):203-223.
Mclaughlin et al., "A Simple, Modular method for the Synthesis of 3,4,5-Trisubstituted Pyrazoles," JOC 2008, 73:4309-4312.
Mercer and Pritchard, "Raf proteins and cancer: B-Raf is identified as a mutational target," Biochim. Biophys. Acta, 2003, 1653:25-40.
Peyssonnaux and Eychene, "The Raf/MEK/ERK pathway: new concepts of activation," Biology of the Cell, 2001, 93:53-62.
Raju et al., "Inhibition of DNA Repair as a Mechanism of Enhanced Radioresponse of Head and Neck Carcinoma Cells by a Selective Cyclooxygenase-2 Inhibitor, Celecoxib," Int. J. Radiation Oncology Biol. Phys., 2005, 53:520-528.
Saulnier et al., "An Efficient method for the Synthesis of Guanidino Prodrugs," Bioorganic and Medicinal Chemistry Letters, 1994, 4:1985.
Sherman et al., "Biologically targeted therapies for thyroid cancers," Thyroid Cancer, Jan. 2011, 329-349.
Takeuchi, Hirofumi, "Strategy for pharmaceutical formulation and new technology," CMC publication, KK, Mar. 31, 2007, pp. 117, 212, 11 pages, with certified English translation.
Tannapfel et al., "Mutations of the BRAF gene in cholangiocardinoma but not the hepatocellular carcinoma," Gut, 2003, 52:706-712.
Tran et al., "Dissolution-modulating mechanism of pH modifiers in solid dispersion containing weakly acidic or basic drugs with poor water solubility," Expert. Opin. Drug Deliv., Dec. 2010, 7(5):647-661.
Trivedi et al., "Novel dihydropyrimidines as a potential new class of antitubercular agents," Bioorganic & medicinal Chemistry Letters, 2010, 20:6100-6102.
Velculescu, "Defining the Blueprint of the Cancer Genome," Carcinogenesis, 2008, 29:1087-1091.
Wellbrock et al., "B-RAF is an Oncogene in Melanocytes," Cancer Res., 2004, 64:2338-2342.
Wojnowski et al., "Endothelial apoptosis in Braf-deficient mice," Nature Genet., 1997, 16:293-297.
Written Opinion in International Application No. PCT/EP2013/073452, dated Dec. 13, 2013, 6 pages.
Written Opinion of the International Searching Authority in International Application No. PCT/EP2009/0595506, dated Sep. 23, 2009, 5 pages.
Written Opinion of the International Searching Authority in International Application No. PCT/EP2011/050654, dated Apr. 6, 2011, 5 pages.
Written Opinion of the International Searching Authority in International Application No. PCT/EP2011/063325, dated Feb. 3, 2013, 6 pages.
Written Opinion of the International Searching Authority in International Application No. PCT/US2010/046930, dated Oct. 9, 2010, 7 pages.
Young et al., "Discovery and evaluation of potent P1 aryl heterocycle-based thrombin inhibitors" J. Med. Chem., 2004. 47:2995-3008.

METHOD OF TREATING COLORECTAL CANCER BY ADMINISTRATION OF PHARMACEUTICAL FORMULATIONS OF (S)-METHYL (1-((4-(3-(5-CHLORO-2-FLUORO-3-(METHYLSULFONAMIDO)PHENY1)-1-ISOPROPYL-1H-PYRAZOL-4-YL)PYRIMIDIN-2-YL)AMINO)PROPAN-2-YL) CARBAMATE

BACKGROUND

This invention relates to solid oral pharmaceutical formulations of (S)-methyl (1-((4-(3-(5-chloro-2-fluoro-3-(methylsulfonamido)phenyl)-1-isopropyl-1H-pyrazol-4-yl)pyrimidin-2-yl)amino)propan-2-yl)carbamate (COMPOUND A) and the use of these formulations for treating proliferative diseases, such as solid tumor diseases.

The COMPOUND A has the chemical structure:

Its preparation and its use as an inhibitor of B-RAF for the treatment of proliferative diseases, such as solid tumor diseases, like melanoma and colorectal cancer, are described in WO 2011/025927, which is here incorporated by reference in its entirety.

COMPOUND A is a BCS class II compound exhibiting poor aqueous solubility at weakly acidic and neutral pH which poses a challenge for oral bioavailability and therapeutic effect. The compound exhibits typical weak base solubility characteristics and is highly soluble at low pH, starts to decline at around pH 3.0 and remains low at intrinsic solubility level over the range of neutral pH. Upon emptying from the stomach, COMPOUND A has the tendency to quickly precipitate out of solution due to an abrupt solubility drop in intestinal pH. This significantly reduces COMPOUND A that is available for intestinal absorption. The present invention relates to orally bioavailable pharmaceutical solid dispersion formulations of COMPOUND A.

DETAILED DESCRIPTION OF THE INVENTION

COMPOUND A is a BCS class II compound which exhibits typical weak base solubility characteristics: higher solubility at low pH, and limited solubility around neutral pH. Therapeutic compounds with such solubility characteristics typically present pharmaceutical formulation scientists with a challenge while attempting to prepare oral formulations capable of improving oral bioavailability of the therapeutic compound. Such challenges in preparing solid oral dosage forms of COMPOUND A are overcome, according to the present invention, by formulating the compound as a solid dispersion.

Solid dispersions are specialized pharmaceutical formulations. The most suitable solid dispersion formulation is the one that enhances solubility and dissolution rate and maintains the stability of the drug substance in an amorphous state. In a typical solid dispersion formulation the drug substance is uniformly dispersed in a solid matrix which promotes dissolution of the drug in the gastrointestinal tract and maintains the drug in a high energy amorphous state.

Pharmaceutical solid dispersions are produced by techniques known in the art, for example, solvent evaporation, kneading and melt extrustion.

According to the present invention, an inner phase is prepared. The inner phase is a solid dispersion comprising COMPOUND A in a suitable polymer matrix, which is composed, for example, of a hydrophilic binder, a surfactant and optional additional excipients, which are known in the art, followed by milling to reduce particle size.

Prior to tableting or encapsulation, the inner phase is preferably combined with additional excipients, which are collectively referred to herein as the external phase. One or more of an acidifier, a filler, a disintegrant, a flow enhancer and a lubricant are typically included in the external phase.

Thus, the present invention relates to a solid oral pharmaceutical formulation which comprises a solid dispersion comprising COMPOUND A.

In one embodiment, the present invention is a solid oral pharmaceutical formulation which comprises:
(a) an inner phase which is a solid dispersion comprising COMPOUND A, and
(b) an external phase which comprises additional excipients.

Preferably, the internal phase, or, more preferably, the external phase comprises an acidifier.

The present invention further relates to a solid oral pharmaceutical formulation which comprises:
(a) an inner phase which is a solid dispersion comprising COMPOUND A, a hydrophilic binder and a surfactant; and
(b) an external phase which comprises additional excipients.

In another embodiment, the present invention is a solid oral pharmaceutical formulation which comprises:
(a) an inner phase which is a solid dispersion comprising COMPOUND A, a hydrophilic binder, a surfactant and
(b) an external phase which comprises one or more of an acidifier, a filler, a disintegrant, a flow enhancer and a lubricant.

The hydrophilic binder should be suitable for complete miscibility with COMPOUND A and upon formulation dissolution, serve as a precipitation inhibitor of COMPOUND A. Suitable hydrophilic binders for inclusion in the inner phase include copovidone, hydroxypropylmethylcellulose, polyvinylpyrrolidone, hydroxypropylcellulose, and methacrylate copolymer, polyethylene oxide, HPMC acetate succinate, HPMC phthalate. Copovidone is especially useful as the hydrophilic binder. KOLLIDON VA64, which is a copolymer of 1-vinyl-2-pyrrolidone and vinyl acetate in a ratio of 6:4 by mass and is available from BASF, is highly suitable for use as a hydrophilic binder in the inner phase.

The surfactant should be suitable for use in melt extrusion to enhance dissolution and solubilization of COMPOUND A. In some cases, the surfactant may help reduce the process temperature through its plasticizing effect. Suitable surfactants for inclusion in the inner phase include poloxamers, such as Poloxamer 188, sodium lauryl sulphate, Tween 80, sorbitol, polysorbate 20, polysorbate 80, Vitamin E TPGS, and polyethylene glycol.

Additional excipients that may optionally be included in the inner phase include acidifiers, and plasticizers.

In the preferred embodiments, the internal phase, or preferably the external phase comprises an acidifier to control the microenvironmental pH in the acidic range. Suitable acidifiers include organic acids such as citric acid, succinic acid, maleic acid, tartaric acid, malic acid and adipic acid.

Suitable fillers, disintegrants, flow enhancers and lubricants are known to those of skill in the art.

Especially useful fillers include lactose, maltodextrin, mannitol, microcrystalline cellulose, pregelatinized starch, and sucrose esters.

Useful disintegrants include crospovidone, croscarmellose sodium, sodium starch glycolate, microcrystalline cellulose, and pregelatinized starch.

Useful flow enhancers include colloidal silicon dioxide, talc, magnesium stearate, and mannitol.

Useful lubricants include magnesium stearate, calcium stearate, glyceryl monostearate, hydrogenated castor oil, sodium lauryl sulfate, sodium stearyl fumarate, stearic acid, zinc stearate, talc, microcrystalline cellulose, and sucrose esters.

In different embodiments of the present invention, the inner phase comprises various ranges of % w/w of active agent, hydrophilic binder and surfactant. For instance, the present inner phase can comprise 5-70% Compound A, 10-90% of hydrophilic binder, and 5-30% surfactant, preferably 5-50% Compound A, 30-80% of hydrophilic binder, and 5-30% surfactant, more preferably 5-40% Compound A, 50-80% of hydrophilic binder, and 5-20% surfactant.

In different embodiments of the present invention, the external phase comprises various ranges of % w/w of acidifier, filler, disintegrant, flow enhancer and lubricant. For instance, the present external phase can comprise 1-70% acidifier, 20-70% filler, 0-30% disintegrant, 0-10% flow enhancer and 0-10% lubricant, preferably 2-60% acidifier, 30-70% filler, 5-20% disintegrant, 0.5-5% flow enhancer and 0.5-5% lubricant, more preferably 10-40% acidifier, 20-40% filler, 1-15% disintegrant, 1-5% flow enhancer and 1-5% lubricant.

In different embodiments of the present invention, the solid oral dosage form, for example, capsules or tablets, are a blend of the internal and external phases in a ratio of from 100:0 to 30:70, preferably 80:20 to 40:60, most preferably 75:25 to 50:50.

Stabilization of an amorphous form of COMPOUND A in a solid dispersion formulation enhances bioavailability, attributable to a higher dissolution rate and kinetic solubility of the amorphous form in comparison to its crystalline form.

When COMPOUND A stays in amorphous form, an increase in kinetic solubility and dissolution rate as well as in oral bioavailability is achieved using the solid dispersion formulation.

In one embodiment, the present invention is formulated as a capsule, such as hard gelatin capsule or a soft elastic capsule. Alternatively, the present invention is in the form of a tablet or a pill. In these solid oral formulations the amount of COMPOUND A can be present in the ranges of 1-1500 mg, 2.5-800 mg, or 5-400 mg, with preferred examples including 10 mg, 20 mg, 25 mg, 50 mg, 100 mg, 200 mg, 400 mg and 500 mg.

The solid oral formulations of the present invention can be administered to treat diseases which respond to inhibition of B-RAF, particularly diseases that are characterized by a mutation in B-RAF, particularly melanoma and colorectal cancer.

Thus, the present invention further relates to the use of a solid oral pharmaceutical formulation described above for the preparation of a medicament for the treatment of a proliferative disease, especially wherein the proliferative disease is a solid tumor disease characterized by a mutation in B-RAF, such as melanoma or colorectal cancer.

The present invention further relates to a method of treating a proliferative disease which comprises administering to a patient in need of treatment a therapeutically effective amount of a formulation described herein, especially wherein the proliferative disease is a solid tumor disease characterized by a mutation in B-RAF, such as melanoma or colorectal cancer.

The following Examples are intended to illustrate, but not to limit, the invention.

Example 1

The following composition is prepared at constant drug loading of 15% and formulated into 10, 25, 50 mg and 100 mg capsules.

| Ingredient | % w/w |
| --- | --- |
| Internal | |
| Compound A | 15 |
| Kollidon VA64 | 45 |
| Pluronic F 68 | 5 |
| External | |
| Succinic acid | 13 |
| Cellulose MKGR | 16 |
| Crosspovidone | 5 |
| Mg Stearate | 0.5 |
| Aerosil | 0.5 |
| Total | 100 |

| Ingredient | 10 mg capsule | 25 mg capsule | 50 mg capsule | 100 mg capsule |
| --- | --- | --- | --- | --- |
| | Internal Phase (mg) | | | |
| Compound A | 10.0 | 25.0 | 50.0 | 100.0 |
| Kollidon VA64 | 29.9 | 74.8 | 150.0 | 300.0 |
| Poloxamer 188 (Pluronic F68) | 3.3 | 8.4 | 16.7 | 33.3 |

-continued

| Ingredient | 10 mg capsule | 25 mg capsule | 50 mg capsule | 100 mg capsule |
|---|---|---|---|---|
| External Phase (mg) | | | | |
| Succinic acid | 8.7 | 21.7 | 43.3 | 86.7 |
| Cellulose microcystalline | 10.7 | 26.7 | 53.3 | 106.7 |
| Crospovidone | 13 | 8.4 | 16.7 | 33.3 |
| Aerosil | 0.3 | 0.9 | 1.7 | 3.3 |
| Magnesium Stearate | 0.3 | 0.9 | 1.7 | 3.3 |
| Total (mg) | 66.6 | 166.5 | 333.4 | 666.6 |

Manufacturing Process:

The processing is performed by hot-melt extrusion using a 18 mm twin-screw Leistriez extruder, followed by milling the extrudates, blending with the external phase and screening. Following blending, the blend is encapsulated into pink hard gelatin capsules of size 0 and 00 for drug doses of 50 and 100 mg respectively. A step-by step approach is shown below:

Weigh the required amount of Compound A, Kollidon VA64 and Poloxamer 188

Blend the mixture

Extrude the blend on a 18 mm Leistreiz twin-screw extruder at a feed rate of 1 kg/hour maintaining temperatures of 50 to 160° C. in the extruder.

Mill the extrudate

Add screened succinic acid and cellulose microcrystalline

Add and blend the milled extrudates, succinic acid and cellulose microcrystalline Add crospovidone and aerosil Blend the mixture Add prescreen magnesium stearate Blend the mixture Encapsulation using H&K encapsulator In-vivo monkey PK data with the resulting capsules show bioavailability suitable for oral administration with a mean Cmax of 11833 ng/ml, Tmax at 4 hours and an AUC of 32686 ng*hr/ml.

XRPD data indicate physical stability of the amorphous solid dispersion formulation (no indication of conversion to the crystalline drug substance) upon storage at accelerated stability conditions of 40° C./75% RH for 4 weeks.

In-vitro 2-stage dissolution studies indicate no change in dissolution kinetics of the solid dispersion between initial (0 week) and 4-week time point at accelerated stability storage conditions indicating no change in physical stability of the solid dispersion.

The present formulation exhibits a glass transition temperature (Tg) of 97° C. which is above the recommended drug product storage temperature of no greater than 30° C., demonstrating physical stability without conversion of the amorphous drug substance into the poorly water soluble crystalline drug substance.

The present formulation shows excellent chemical stability upon storage at accelerated stability conditions at 40° C./75% RH with no evidence of any degradation products and 100% assay content results for COMPOUND A.

Example 2

The following formulation is prepared in a manner similar to that described in Example 1.

| Ingredient | % w/w |
|---|---|
| Internal | |
| LGX818 | 17 |
| PVP-K30 | 51 |
| Sorbitol | 5 |
| External | |
| Succinic Acid | 9 |
| Cellulose MKGR | 12 |
| Crosspovidone | 5 |
| Mg Stearate | 0.5 |
| Aerosil | 0.5 |
| Total | 100 |

This formulation exhibits a glass transition temperature (Tg) of 109° C. demonstrating physical stability without conversion of the amorphous drug substance into the poorly water soluble crystalline drug substance.

Example 3

The following table described the results of a pharmacokinetic study in monkeys of Compound A formulated as a microemulsion dosed at 50 mg/kg and the formulations of Example 1 (Solid Dispersion 1) and Example 2 (Solid Dispersion 2) at a dose of 200 mg of Compound A.

| Treatment_ID | Subject_ | Tmax (h) | Cmax ng/mL | AUClast ng * h/mL | Tlast (h) |
|---|---|---|---|---|---|
| Microemulsion (early) | monkey 1 | 2 | 2510 | 21000 | 30 |
| 1 | monkey 2 | 4 | 3410 | 25400 | 30 |
| | monkey 3 | 4 | 727 | 8820 | 30 |
| | Mean | 3.3 | 2216 | 18407 | |
| | SD | 1.2 | 1366 | 8589 | |
| Solid Dispersion_1 | monkey 1 | 4 | 9830 | 42377 | 30 |
| (Kollidon) | monkey 2 | 2 | 13500 | 35816 | 30 |
| Showed emesis | monkey 3 | 2 | 10600 | 24626 | 30 |
| | monkey 4 | 2 | 271 | 1037 | 8 |
| | monkey 5 | 8 | 13400 | 27924 | 24 |
| | Mean | | 11833 | 32686 | |
| | SD | | 1894 | 7986 | |
| Solid Dispersion_2 | monkey 1 | 2 | 18100 | 43327 | 30 |
| (PVP-K30) | monkey 2 | 2 | 13000 | 29756 | 30 |
| | monkey 3 | 2 | 2220 | 5804 | 30 |
| | monkey 4 | 1 | 14500 | 33177 | 30 |
| | monkey 5 | 1 | 12900 | 21390 | 30 |
| | Mean | | 12144 | 26691 | |
| | SD | | 5933 | 14076 | |

Examples 2-7

Figure 1:
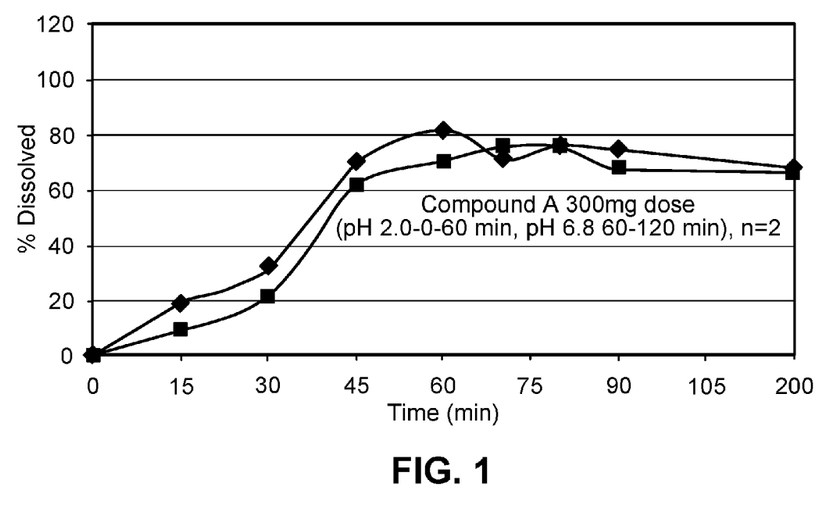
FIG. 1 represents the 2 stage dissolution profile of the formulation described in Example 1.
Figure 2:
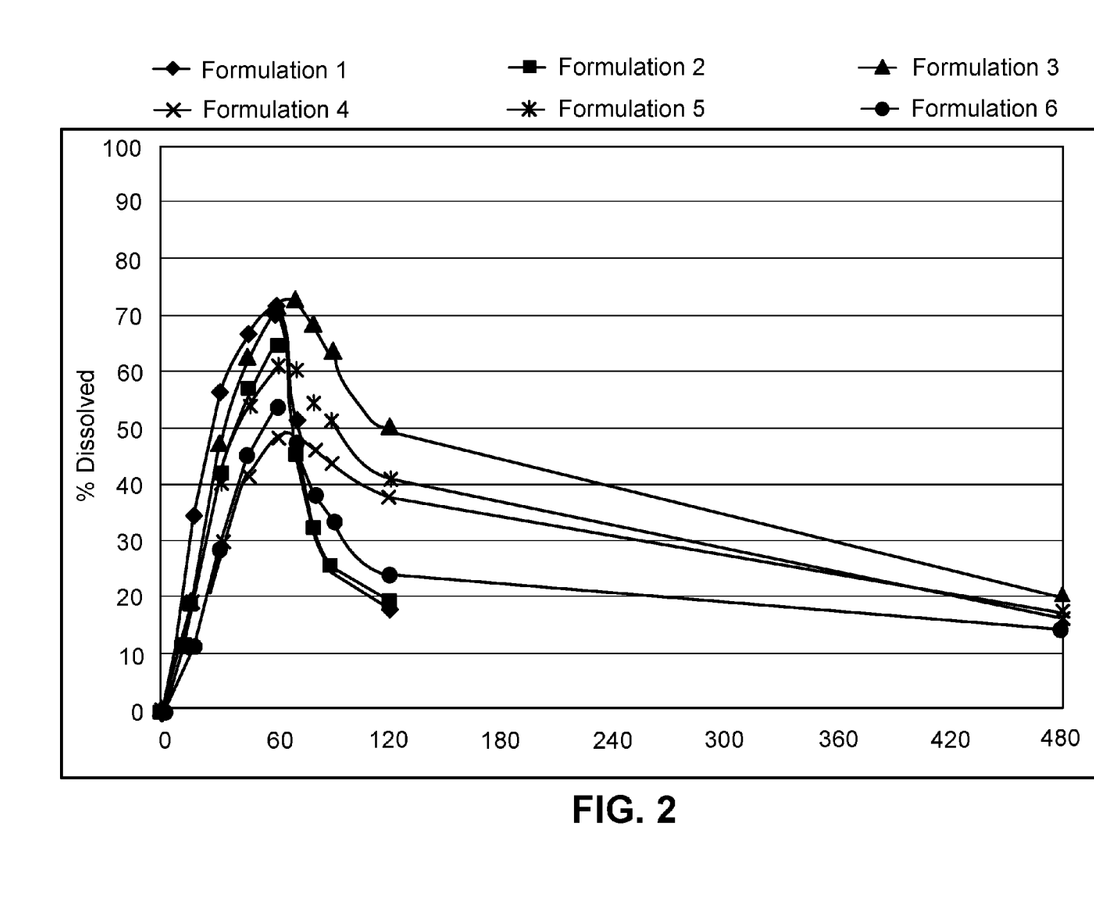
FIG. 2 represents the 2-Stage (pH 2 first 60 min to 6.8 after 60 min) dissolution of the formulations described in Examples 2-7.

The following formulations are prepared by techniques similar to those described in Example 1, but with a single phase. The dissolution profiles of the formulations are reported in FIG. 2.

Formulation 2:

| Ingredients | % W/W |
| --- | --- |
| Compound A | 25.00 |
| Vitamin E TPGS | 41.67 |
| Polyethylene glycol 4000 | 26.33 |
| Hydroxypropylmethyl cellulose | 5.00 |
| Talc | 2.00 |

Formulation 3:

| Ingredients | % W/W |
| --- | --- |
| Compound A | 25.00 |
| Vitamin E TPGS | 41.67 |
| Polyethylene glycol 4000 | 16.33 |
| Hydroxypropylmethyl cellulose | 15.00 |
| Talc | 2.00 |

Formulation 4:

| Ingredients | % W/W |
| --- | --- |
| Compound A | 25.00 |
| Vitamin E TPGS | 41.67 |
| Polyethylene glycol 4000 | 5.92 |
| Hydroxypropylmethyl cellulose | 15.00 |
| Maleic acid | 5.41 |
| Eudragit L100-55 | 5.00 |
| Talc | 2.00 |

Formulation 5:

| Ingredients | % W/W |
| --- | --- |
| Compound A | 25.00 |
| Vitamin E TPGS | 41.67 |
| Polyethylene glycol 4000 | 5.92 |
| Hydroxypropylmethyl cellulose | 5.00 |
| Maleic acid | 5.41 |
| Eudragit L100-55 | 15.00 |
| Talc | 2.00 |

Formulation 6:

| Ingredients | % W/W |
| --- | --- |
| Compound A | 24.00 |
| Vitamin E TPGS | 40.00 |
| Hydroxypropylmethyl cellulose | 14.40 |
| Maleic acid | 5.20 |
| Eudragit L100-55 | 14.40 |
| Talc | 2.00 |

Formulation 7:

| Ingredients | % W/W |
| --- | --- |
| Compound A | 24.00 |
| Vitamin E TPGS | 40.00 |
| Polyethylene glycol 4000 | 1.20 |
| Hydroxypropylmethyl cellulose | 14.40 |
| Lactic acid | 4.00 |
| Eudragit L100-55 | 14.40 |
| Talc | 2.00 |

Example 8

Figure 3:
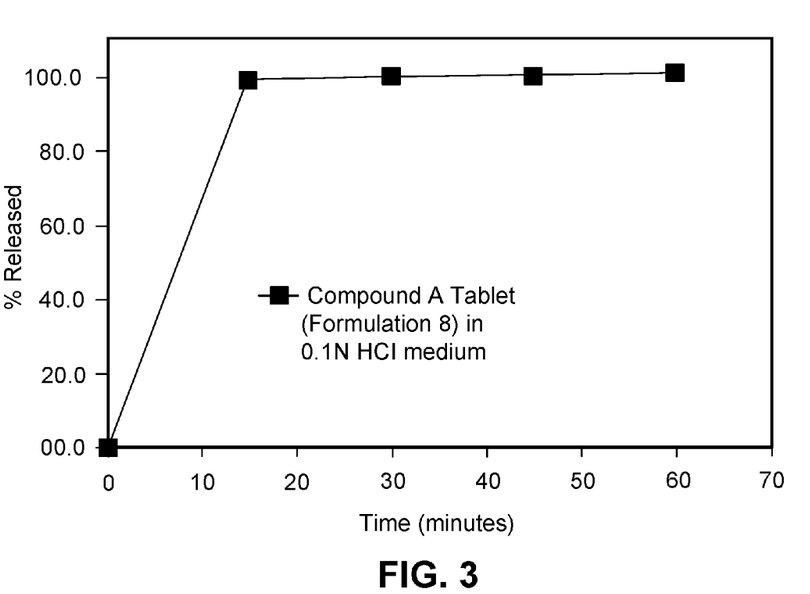
FIG. 3 represents the dissolution profile of the tablet formulation described in Example 8.

The following formulation is prepared by techniques similar to those described in Example 1, but in a tablet dosage form. The dissolution profile of the formulation in 0.1N HCl medium is reported in FIG. 3.

Formulation 8:

| Ingredient | % w/w |
| --- | --- |
| Internal | |
| Compound A | 10.0 |
| Kollidon VA64 | 30.1 |
| Pluronic F 68 | 3.4 |
| External | |
| Kollidon VA64 | 3.0 |
| Cellulose MKGR | 37.5 |
| Crospovidone | 15.0 |
| Mg Stearate | 1.0 |
| Total | 100 |

We claim:

1. A method for treating colorectal cancer, the method comprising administering to a patient in need of treatment a therapeutically effective amount of a solid oral pharmaceutical formulation, wherein the formulation comprises:
    an inner phase which is a solid dispersion comprising amorphous (S)-methyl (1-((4-(3-(5-chloro-2-fluoro-3-(methylsulfonamido)phenyl)-1-isopropyl-1H-pyrazol-4-yl)pyrimidin-2-yl)amino)propan-2-yl)carbamate (COMPOUND A); copovidone; and poloxamer 188 or sorbitol; and
    an external phase which comprises succinic acid, microcrystalline cellulose, crospovidone, colloidal silicon dioxide, and magnesium stearate.

2. The method of claim 1, wherein the colorectal cancer is characterized by a mutation in B-RAF.

3. The method of claim 1, wherein the inner phase comprises from 5% to 40% by weight of amorphous (S)-methyl (1-((4-(3-(5-chloro-2-fluoro-3-(methyl sulfonamido)phenyl)-1-isopropyl-1H-pyrazol-4-yl)pyrimidin-2-yl)amino)propan-2-yl)carbamate (Compound A), from 50% to 80% by weight of copovidone, and from 5% to 20% by weight of poloxamer 188 or sorbitol.

4. The method of claim 1, wherein the external phase comprises from 2% to 60% by weight of succinic acid, from 30% to 70% by weight of microcrystalline cellulose, from 5% to 20% by weight of crospovidone, from 0.5% to 5% by weight of colloidal silicon dioxide, and from 0.5% to 5% by weight of magnesium stearate.

5. The method of claim 1, comprising a blend of the internal and external phases in a ratio of from 80:20 to 40:60.

6. The method of claim 5, comprising a blend of the internal and external phases in a ratio of from 75:25 to 50:50.

7. The method of claim 1, wherein the formulation comprises 10 mg, 25 mg, 50 mg, or 100 mg of amorphous (S)-methyl (1-((4-(3-(5-chloro-2-fluoro-3-(methyl sulfonamido)phenyl)-1-isopropyl-1H-pyrazol-4-yl)pyrimidin-2-yl)amino)propan-2-yl)carbamate (Compound A).

8. The method of claim 7, wherein the formulation comprises 50 mg of amorphous (S)-methyl (1-((4-(3-(5-chloro-2-fluoro-3-(methylsulfonamido)phenyl)-1-isopropyl-1H-pyrazol-4-yl)pyrimidin-2-yl)amino)propan-2-yl)carbamate (Compound A).

9. The method of claim 7, wherein the formulation comprises 15% by weight of amorphous (S)-methyl (1-((4-(3-(5-chloro-2-fluoro-3-(methylsulfonamido)phenyl)-1-isopropyl-1H-pyrazol-4-yl)pyrimidin-2-yl)amino)propan-2-yl)carbamate (Compound A).

10. The method of claim 1, wherein the formulation is selected from the group consisting of:

A)

| Ingredient | % w/w |
| --- | --- |
| Internal Phase | |
| amorphous (S)-methyl (1-((4-(3-(5-chloro-2-fluoro-3-(methylsulfonamido)phenyl)-1-isopropyl-1H-pyrazol-4-yl)pyrimidin-2-yl)amino)propan-2-yl)carbamate (Compound A) | 15 |
| copovidone | 45 |
| Poloxamer 188 | 5 |
| External Phase | |
| Succinic acid | 13 |
| Microcrystalline cellulose | 16 |
| Crosspovidone | 5 |
| magnesium Stearate | 0.5 |
| Colloidal silicon dioxide | 0.5 |
| Total | 100 | and

B)

| Ingredient | % w/w |
| --- | --- |
| Internal | |
| amorphous (S)-methyl (1-((4-(3-(5-chloro-2-fluoro-3-(methylsulfonamido)phenyl)-1-isopropyl-1H-pyrazol-4-yl)pyrimidin-2-yl)amino)propan-2-yl)carbamate (Compound A) | 17 |
| PVP-K30 | 51 |
| Sorbitol | 5 |
| External | |
| Succinic Acid | 9 |
| Microcrystalline cellulose | 12 |
| Crosspovidone | 5 |
| Mg Stearate | 0.5 |
| Colloidal silicon dioxide | 0.5 |
| Total | 100. |

11. The method of claim 10, wherein the colorectal cancer is characterized by a mutation in B-RAF.

12. The method of claim 1, wherein the formulation is

| Ingredient | % w/w |
| --- | --- |
| Internal Phase | |
| amorphous (S)-methyl (1-((4-(3-(5-chloro-2-fluoro-3-(methylsulfonamido)phenyl)-1-isopropyl-1H-pyrazol-4-yl)pyrimidin-2-yl)amino)propan-2-yl)carbamate (Compound A) | 15 |
| copovidone | 45 |
| Poloxamer 188 | 5 |
| External Phase | |
| Succinic acid | 13 |
| Microcrystalline cellulose | 16 |
| Crosspovidone | 5 |
| magnesium Stearate | 0.5 |
| Colloidal silicon dioxide | 0.5 |
| Total | 100. |

13. The method of claim 12, wherein the colorectal cancer is characterized by a mutation in B-RAF.

14. The method of claim 1, wherein the formulation is selected from the group consisting of:

| Ingredient | |
| --- | --- |
| Internal Phase (mg) | |
| amorphous (S)-methyl (1-((4-(3-(5-chloro-2-fluoro-3-(methylsulfonamido)phenyl)-1-isopropyl-1H-pyrazol-4-yl)pyrimidin-2-yl)amino)propan-2-yl)carbamate (Compound A) | 10.0 |
| Copovidone | 29.9 |
| Poloxamer 188 | 3.3 |
| External Phase (mg) | |
| Succinic acid | 8.7 |
| Cellulose microcrystalline | 10.7 |
| Crospovidone | 3.3 |
| Colloidal silicon dioxide | 0.3 |
| Magnesium Stearate | 0.3 |
| Total (mg) | 66.6, |

| Ingredient | |
| --- | --- |
| Internal Phase (mg) | |
| amorphous (S)-methyl (1-((4-(3-(5-chloro-2-fluoro-3-(methylsulfonamido)phenyl)-1-isopropyl-1H-pyrazol-4-yl)pyrimidin-2-yl)amino)propan-2-yl)carbamate (Compound A) | 25.0 |
| Copovidone | 74.8 |
| Poloxamer 188 | 8.4 |
| External Phase (mg) | |
| Succinic acid | 21.7 |
| Cellulose microcrystalline | 26.7 |
| Crospovidone | 8.4 |
| Colloidal silicon dioxide | 0.9 |
| Magnesium Stearate | 0.9 |
| Total (mg) | 166.5, |

| Ingredient | |
|---|---|
| Internal Phase (mg) | |
| amorphous (S)-methyl (1-((4-(3-(5-chloro-2-fluoro-3-(methylsulfonamido)phenyl)-1-isopropyl-1H-pyrazol-4-yl)pyrimidin-2-yl)amino)propan-2-yl)carbamate (Compound A) | 50.0 |
| Copovidone | 150.0 |
| Poloxamer 188 | 16.7 |
| External Phase (mg) | |
| Succinic acid | 43.3 |
| Cellulose microcrystalline | 53.3 |
| Crospovidone | 16.7 |
| Colloidal silicon dioxide | 1.7 |
| Magnesium Stearate | 1.7 |
| Total (mg) | 333.4, | and

| Ingredient | |
|---|---|
| Internal Phase (mg) | |
| amorphous (S)-methyl (1-((4-(3-(5-chloro-2-fluoro-3-(methylsulfonamido)phenyl)-1-isopropyl-1H-pyrazol-4-yl)pyrimidin-2-yl)amino)propan-2-yl)carbamate (Compound A) | 100.0 |
| Copovidone | 300.0 |
| Poloxamer 188 | 33.3 |
| External Phase (mg) | |
| Succinic acid | 86.7 |
| Cellulose microcrystalline | 106.7 |
| Crospovidone | 33.3 |
| Colloidal silicon dioxide | 3.3 |
| Magnesium Stearate | 3.3 |
| Total (mg) | 666.6. |

15. The method of claim 14, wherein the colorectal cancer is characterized by a mutation in B-RAF.

16. The method of claim 1, wherein the formulation is:

| Ingredient | |
|---|---|
| Internal Phase (mg) | |
| amorphous (S)-methyl (1-((4-(3-(5-chloro-2-fluoro-3-(methylsulfonamido)phenyl)-1-isopropyl-1H-pyrazol-4-yl)pyrimidin-2-yl)amino)propan-2-yl)carbamate (Compound A) | 50.0 |
| Copovidone | 150.0 |
| Poloxamer 188 | 16.7 |
| External Phase (mg) | |
| Succinic acid | 43.3 |
| Cellulose microcrystalline | 53.3 |
| Crospovidone | 16.7 |
| Colloidal silicon dioxide | 1.7 |
| Magnesium Stearate | 1.7 |
| Total (mg) | 333.4. |

17. The method of claim 14, wherein the colorectal cancer is characterized by a mutation in B-RAF.

18. The method of claim 1, wherein the formulation is formulated as a capsule or a tablet.

19. The method of claim 10, wherein the formulation is formulated as a capsule or a tablet.

20. The method of claim 12, wherein the formulation is formulated as a capsule or a tablet.

21. The method of claim 14, wherein the formulation is formulated as a capsule or a tablet.

22. The method of claim 16, wherein the formulation is formulated as a capsule or a tablet.

* * * * *